United States Patent [19]

Bitonti

[11] Patent Number: 5,610,171
[45] Date of Patent: *Mar. 11, 1997

[54] INHIBITION OF METASTASIS IN PATIENTS HAVING CANCER WITH PYRIDYLOXAZOLE-2-ONES

[75] Inventor: Alan J. Bitonti, Cincinnati, Ohio

[73] Assignee: Merrell Pharmaceuticals Inc., Cincinnati, Ohio

[ * ] Notice: The term of this patent shall not extend beyond the expiration date of Pat. No. 5,182,293.

[21] Appl. No.: 368,253

[22] Filed: Jan. 3, 1995

Related U.S. Application Data

[63] Continuation of Ser. No. 54,464, Apr. 28, 1993, abandoned, which is a continuation of Ser. No. 890,321, May 26, 1992, abandoned, which is a continuation of Ser. No. 699,821, May 14, 1991, abandoned.

[51] Int. Cl.$^6$ ............................ A61K 31/44; A61K 31/42
[52] U.S. Cl. ............................................. 514/340; 514/376
[58] Field of Search ..................................... 514/376, 908, 514/471, 772, 340

[56] References Cited

U.S. PATENT DOCUMENTS

| | | | |
|---|---|---|---|
| 4,670,450 | 6/1987 | Schnettler et al. | 514/341 |
| 4,698,353 | 10/1987 | Schnettler et al. | 514/340 |
| 4,728,661 | 3/1988 | Schnettler et al. | 514/376 |
| 4,866,085 | 9/1989 | Schnettler et al. | 514/376 |
| 5,182,293 | 1/1993 | Sunkara | 514/340 |

FOREIGN PATENT DOCUMENTS

| | | | |
|---|---|---|---|
| 2935902 | 6/1989 | Germany | C07D 263/38 |

OTHER PUBLICATIONS

B. Krieg, et al., 4–Oxazolin–2–One Aus N–(2–Oxoalkyl)–1–Imidazolcarboxamiden, *Liebigs Ann. Chem.*, 1862–1872 (1976).

Robinson et al, Biosis Abstract 91:94846 of J. Pharmacol. Exp. Ther. 255(3):1392–1398 (1990).

*Primary Examiner*—Raymond Henley, III
*Attorney, Agent, or Firm*—Michael J. Sayles

[57] ABSTRACT

This invention is directed to pyridinyloxazole-2-ones which are useful in inhibiting metastasis in patients having cancer. The pyridinyloxazole-2-ones act to inhibit protein kinase C and thereby modulate metastasis in patients having cancer.

7 Claims, No Drawings

INHIBITION OF METASTASIS IN PATIENTS HAVING CANCER WITH PYRIDYLOXAZOLE-2-ONES

This is a continuation of application Ser. No. 08/054,464, filed Apr. 28, 1993, now abandoned, which is a continuation of application Ser. No. 07/890,321, filed May 26, 1992, now abandoned; which is a continuation of application Ser. No. 07/699,821, filed May 14, 1991, now abandoned, which is herein incorporated by reference.

This invention relates to the use of certain pyridinyloxazole-2-ones as inhibitors of protein kinase C to inhibit metastasis in patients having cancer.

BACKGROUND OF THE INVENTION

Phorbol esters which activate protein kinase C (PKC) have been shown to enhance experimental lung metastasis. Therefore, it was logical that inhibitors of PKC might also modulate metastasis. The later possibility was investigated with the pyridyloxazole-2-one, 4-propyl-5(4-pyridinyl)-2(3H)-oxazolone, as well as with the PKC inhibitors H-7 and staurosporine.

SUMMARY OF THE INVENTION

The present invention is directed to the use of certain pyridinyloxazole-2-ones of the formula

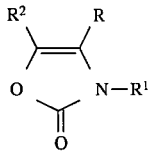

wherein

R and $R^1$ are each independently selected from the group consisting of hydrogen, $C_1$–$C_6$ alkyl, and phenyl or $C_1$–$C_3$ alkylphenyl wherein the phenyl ring is optionally substituted with one, two or three of the substituents selected from the group consisting of fluorine, chlorine, bromine, $C_1$–$C_4$ alkyl, and $C_1$–$C_4$ alkoxy; and $R^2$ is a 2-, 3-, or 4-pyridyl group wherein the pyridyl group is optionally substituted with one or two substituents selected from the group consisting of fluorine, chlorine, bromine, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, cyano, carboxy, carb($C_1$–$C_5$)alkoxy, carbamido, ($C_1$–$C_5$)alkanoylamino, imidazolyl, nitro and trifluoromethyl or wherein the pyridyl group is optionally substituted with a phenyl group which is optionally substituted with one, two or three of the substituents selected from the group consisting of fluorine, chlorine, bromine, $C_1$–$C_4$ alkyl, and $C_1$–$C_4$ alkoxy;

and the pharmaceutically-acceptable salts thereof in treating patients with cancer to inhibit metastasis.

Treatment of B16F1 murine melanoma cells with 4-propyl-5(4-pyridinyl)-2(3H)-oxazolone for 24 hours in culture and subsequent intravenous injection of the cells into C57BL/6 mice resulted in 90% inhibition of lung metastasis. Viability of treated cells was shown to be equivalent to untreated cells by use of [$^3$H]-thymidine incorporation and by a clonogenic assay. The inhibition of metastasis was time dependent with 50% of maximum inhibition occurring by 8 hours of incubation. The $IC_{50}$ for inhibition of metastasis with 4-propyl-5(4-pyridinyl)-2(3H)-oxazolone was 7 µM which correlated with the inhibition of B16F1 membrane-associated PKC ($IC_{50}$=13 µM) but not with inhibition of cytosolic PKC ($IC_{50}$=54 µM). B16F1 cells treated with 4-propyl-5(4-pyridinyl)-2(3H)-oxazolone for 24 hours were less adherent than untreated cells when attachment to extracellular matrix/basement membrane proteins was examined. Adhesion to fibrinogen and collagen IV were the most sensitive to inhibition with 4-propyl-5(4-pyridinyl)-2(3H)-oxazolone whereas adherence to laminin and fibronection was inhibited minimally or not at all, indicating a specificity in the drug response. B16F1 cells treated with 4-propyl-5(4-pyridinyl)-2(3H)-oxazolone were also found to be less adherent to human umbilical vein endothelial cells (HUVEC). It was found that 4-propyl-5(4-pyridinyl)-2(3H)-oxazolone was more potent than H-7 for the inhibition of metastasis and adhesion but was significantly less potent than staurosporine. Neither H-7 nor staurosporine inhibited adherence of the B16F1 cells to either fibrinogen, collagen IV or to HUVEC, suggesting a novel mechanism for 4-propyl-5(4-pyridinyl)-2(3H)-oxazolone. Our results support the hypothesis that there is a role for PKC-mediated phosphorylation of cell surface adhesion receptors in metastasis.

DETAILED DESCRIPTION OF THE INVENTION

This invention concerns the use of the compounds of Formula I as agents effective in inhibiting metastasis in patients having cancer.

As used herein, the terms "$C_1$–$C_3$ alkyl", "$C_1$–$C_4$ alkyl" and "$C_1$–$C_6$ alkyl" mean straight or branched chain alkyl groups having from one to three, from one to four, or from one to six carbon atoms respectively, and include such groups as methyl, ethyl, n-propyl, isopropyl, n-butyl, isobutyl, sec-butyl, tert-butyl, and the like, as well as vinyl, allyl, propenyl, butenyl, butadienyl, isopropenyl, and the like. The term "$C_1$–$C_4$ alkoxy" means alkoxy groups having from one to four carbon atoms, and includes such groups as methoxy, ethoxy, n-propoxy, isopropoxy, n-butoxy, isobutoxy, sec-butoxy, tert-butoxy, and the like. When R or $R^1$ is "optionally substituted phenyl or $C_1$–$C_3$ alkylphenyl", the one two or three substituent(s) can be located at any available position on the phenyl ring.

The expression "a pharmaceutically acceptable acid addition salt" is intended to apply to any nontoxic organic or inorganic acid addition salt of the base compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are,for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Illustrative examples of the compounds of this invention include compounds of Formula I wherein the R groups are designated as follows:

| R | $R^1$ | $R^2$ |
|---|---|---|
| hydrogen | hydrogen | 2-,3-, or 4-pyridinyl |
| ethyl | hydrogen | 2-,3-, or 4-pyridinyl |
| propyl | hydrogen | 5-,6-, 7- or 8-pyridinyl |
| methyl | benzyl | 2-,3- or 4-pyridinyl |
| phenethyl | hydrogen | 2-,3-, or 4-pyridinyl |
| phenyl | hydrogen | 2-,3- or 4-pyridinyl |
| propyl | hydrogen | 2-,3- or 4-(6,7-dimethyl)-pyridinyl |
| propyl | hydrogen | 2-,3-, or 4-(6-phenyl)-pyridinyl |
| 4-methoxyphenethyl | hydrogen | 2,3- or 4-pyridinyl |
| 4-methoxyphenyl | hydrogen | 2,3- or 4-pyridinyl |
| benzyl | benzyl | 2-,3- or 4-(7-ethoxy)-pyridinyl |
| phenyl | phenyl | 2-,3- or 4-(7-ethoxy)-pyridinyl |
| phenyl | phenyl | 2-,3-, or 4-(7-phenyl)-pyridinyl |
| butyl | hydrogen | 2-,3- or 4-pyridinyl |
| 3,5-dichloro-phenylpropyl | methyl | 5-,6-,7- or 8-pyridinyl |
| 3,5-dichloro)phenyl | methyl | 5-,6-,7- or 8-pyridinyl |
| propyl | methyl | 2-,3- or 4-pyridinyl |
| 3,5-dimethoxybenzyl | ethyl | 5-,6-,7- or 8-pyridinyl |
| 3,5-dimethoxyphenyl | ethyl | 5-,6-,7- or 8-pyridinyl |
| methyl | propyl | 2-,3- or 4-(5-ethoxy-7-methyl)-pyridinyl |
| butyl | butyl | 5-,6-,7- or 8-pyridinyl |
| hydrogen | phenethyl | 2-,3- or 4-(6-trifluoromethyl)-pyridinyl |
| hydrogen | phenethyl | 2-,3-, or 4-(6-phenyl)-pyridinyl |
| methyl | 4-methoxy-phenethyl | 2-,3- or 4-pyridinyl |

As is true for most classes of therapeutically effective compounds, certain subclasses and certain species are especially effective and are preferred over others. In this instance, those compounds of Formula I wherein $R^2$ is optionally substituted 2-, 3-, or 4-pyridinyl are preferred. Also preferred are compounds wherein R is hydrogen or a $C_1$–$C_6$ alkyl. Most preferred are the compounds wherein $R^2$ is an unsubstituted 2-, 3-, or 4-pyridinyl group, R is propyl and $R^1$ is hydrogen. The most preferred compound of this invention is 4-propyl-5-(4-pyridinyl)-2(3H)-oxazolone.

The preparation of the 2-, 3-, or 4-pyridinyloxazole-2-ones of this invention is known in the art. See for example, U.S. Pat. No. 4,698,353. The preparation of those compounds not specifically taught in the art can be readily accomplished by the skilled artisan.

In essence, the compounds of this invention can be prepared by reacting a compound of formula 2

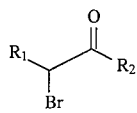

(2)

wherein $R_1$ and $R_2$ are as defined above with a cyanate in DMF to form the corresponding isocyanate which undergoes cyclization under the reaction conditions to yield the desired formula 1 product.

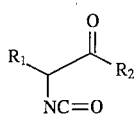

(3)

Another procedure involves cyclizing a hydroxy ketone of structure 4

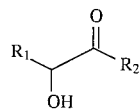

(4)

wherein $R_1$ and $R_2$ are as defined above by reaction with a cyanate or salt in the presence of an acid.

The bromo ketones of formula 2 are either known in the art or can be readily prepared by standard techniques. For example the des-bromo analog of a structure 2 compound can be treated with bromine. Where the group adjacent to the carbon to be brominated is a hydrogen or a ($C_1$–$C_5$) alkyl group, a radical initiator can be used to promote the bromination. Suitable initiators include iron metal and N-bromosuccinimide. The bromination can also be accomplished by the addition of concentrated hydrobromic acid, typically 48% aqueous hydrobromic acid, to a solution containing desbromo compound. The structure (4) hydroxy ketones can also be readily prepared in any suitable manner. For example, a structure 2 bromo ketone can be allowed to react with an acetate salt, preferably potassium acetate, to form the corresponding acetoxy ketone which upon treatment with an acid, such as hydrochloric acid, yields the desired structure (4) compound.

The compounds wherein R is $C_1$–$C_6$ alkyl or optionally substituted phenyl or $C_1$–$C_3$ alkylphenyl are produced by subsequent reaction of the compound of Formula 1 wherein R is hydrogen with sodium hydride and the appropriate alkyl iodide or phenylalkyl iodide in tetrahydrofuran according to procedures well known in the art.

The compounds of this invention are useful both in the free base form and as salts. The expression "pharmaceutically-acceptable salt" means any organic or inorganic addition salt of the base compounds of Formula I which are relatively nontoxic and innocuous to a patient at concentrations consistent with effective activity so that the side effects ascribable to the salt do not vitiate the beneficial effects of the base compounds of Formula I. These salts are included within the scope of this invention. Such salts include alkali metal salts, such as sodium and potassium salts and alkaline earth metal salts, such as calcium and magnesium salts; and the like. Also salts with organic and inorganic acids can be prepared, such as, for example, those formed with the following acids: hydrochloric, hydrobromic, sulfonic, sulfuric, phosphoric, nitric, ascorbic, methanesulfonic, acetic, propionic, tartaric, citric, lactic, malic, mandelic, cinnamic, palmitic, itaconic, fumaric, benzenesulfonic and toluenesulfonic. The nontoxic, physiologically acceptable salts are preferred, although other salts are also useful, for example, in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying, or by exchanging the cations of an existing salt for another cation on a suitable ion exchange resin.

Cell adhesion is an important factor in tumor metastasis. Cells escape from the primary tumor into the circulation through loss of adhesive properties, while the arrest and establishment of a new colony is dependent upon the development of increased ability of these cells to adhere to endothelial cells lining the vasculature or to the extracellular matrix proteins. These events in the metastatic cascade have to involve a down-regulation of cell adhesion receptors for extravasation followed by an up-regulation for the attachment of cells at their final destination. Cell adhesion receptors called integrins have been associated with tumorigenicity and metastasis. These receptors are cell surface glycoproteins that bind to basement membrane proteins, such as fibrinogen, fibronectin, laminin and collagen, with relatively low affinity. Small peptides containing an arginine-glycine-aspartate (RGD) sequence, a binding sequence found in the adhesion proteins, inhibit the normal function of integrins. The importance of integrins to metastasis has been inferred in experiments in which large amounts of RGD peptides were injected simultaneously with tumor cells into mice resulting in a decreased number of metastatic foci. In addition, changes in structure or expression of integrins have been linked to cells that have acquired a malignant phenotype.

Phosphorylation of protein receptors often induces conformational changes in the protein which can affect binding characteristics to its ligand. Protein kinases phosphorylate integrins and a host of other cellular proteins. Protein kinase C is particularly interesting since its activation has been associated with increased adherent potential and increased metastatic activity of tumor cells. This calcium-activated and phospholipid-dependent kinase mediates signal transduction for the secretion and release of growth factors, hormones, proteases and neurotransmitters. Coupling of these stimuli to their membrane receptors causes the breakdown of phosphoinositides into diacylglycerol and inositol triphosphate. Diacylglycerol activates PKC which in turn catalyzes the phosphorylation of specific proteins. Inositol triphosphate causes the release of calcium from the endoplasmic reticulum, also contributing to the activation of the kinase. In addition, PKC is the major intracellular receptor for the phorbol esters tumor promoters which bind to and activate the enzyme in an analogous manner to diacylglycerol.

Tumor promoters and compounds that activate calcium mobilization have been shown to increase metastasis in experimental animal models and also enhance the adherence potential of tumor cells. Treatment of B16 murine melanoma cells in vitro with phorbol-12-myristate-13-acetate (PMA) and subsequent intravenous injection into mice resulted in increased numbers of metastatic foci in lungs. In a murine model of spontaneous metastasis, SP1 mouse mammary adenocarcinoma cells, in which the cells normally do not metastasize, treatment with either PMA or the calcium ionophor A23187 resulted in metastasis from the primary tumor. In addition, Lewis lung carcinoma cells treated with PMA results in an enhancement of adhesion to endothelial cells. It is logical, therefore, that inhibition of PKC may reduce the metastatic potential of tumor cells. In the study presented here in this application, we have investigated the effect of 4-propyl-5(4-pyridinyl)-2(3H)-oxazolone, and other novel PKC inhibitors in an experimental metastasis model. Exposure of B16F1 melanoma cells to 4-propyl-5(4-pyridinyl)-2(3H)-oxazolone in vitro diminished the number of lung metastases when treated cells were injected subsequently into mice. In addition, B16F1 cells treated with this drug showed decreased adhesion to some basement membrane proteins and to vascular endothelial cells in vitro. It is suggested that the drug through inhibition of PKC, affects cell adhesion properties that are related to integrin phosphorylation.

MATERIALS AND METHODS

Cell Culture

B16F1 cells (American Tissue Culture Collection #6323) were cultured in Minimal Essential Medium (MEM) supplemented with 10% fetal bovine serum (FBS), 2 µM L-glutamine and 5 µg gentamycin per liter.

Human umbilical vein endothelial cells (HUVEC) were obtained from Clonetics Corporation and cultured as monolayers using Endothelial Growth Medium-Umbilical Vein (EGM-UV) supplied with cells.

Colony Forming Assay

One hundred viable cells, as determined by trypan blue exclusion, were plated per 35 mm dish in MEM and incubated for 24 hours at 37° C. Next, 4-propyl-5(4-pyridinyl)-2(3H)-oxazolone was added and incubation continued for an additional 24 hours, after which the dishes were washed twice with Hank's Balanced Salt Solution (HBSS) and replenished with MEM. Ten days later, colonies with a diameter of 2 mm or greater were counted.

Experimental Metastasis Assay

Sub-confluent B16F1 cells were harvested by washing with HBSS followed by trypsinization for 1 minute. The cells were sedimented by centrifugation (250 g, 5 minutes) and washed twice with HBSS. Viable cells were counted after dilution with trypan blue. A single-cell suspension of $10^5$ cells in 0.2 ml HBSS was injected intravenously into 16–18 C57BL/6 mice via the tail vein. Three weeks later, the number of metastatic foci in the lung were counted.

Protein Kinase C Preparation

Cytostolic and membrane-associated PKC was prepared as described in Thomas, T. P., Gopalakrishna, R. and Anderson, W. B. Hormone- and tumor promoter-induced activation of membrane association of protein kinase C in intact cells, *Methodsin Enzymology*, 141: 399–411, 1987. Sub-confluent B16F1 cultures ($4 \times 10^7$ cells total) were washed twice with phosphate buffered saline (PBS), pH 7.2 and then twice with buffer A (20 mM Tris, pH 7.5, 2 mM EDTA, 0.5 mM EGTA, 0.33 mM sucrose, 2 mM phenylmethylsulfonyl fluoride (PMSF), and 2 µg/ml leupeptin). Cells were scraped from the plates in buffer A, homogenized (40 strokes) and sedimented by centrifugation for 1 hour at 100,000 g. The cytosol was stored on ice while the particulate fraction was washed with buffer B (20 mM Tris, pH 7.2, 2 mM EDTA, 0.5 mM EGTA, and 2 mM (PMSF). The membranes were resuspended with buffer B and homogenized with 10 strokes. Nonidet P-40 (1% final concentration) was added and the mixture was incubated for 30 minutes at 4° C. in a rotating mixer. Nonsolubilized material was removed by centrifugation for 10 minutes at 1400 g. Cytostolic and membrane-bound PKC was partially purified by chromatography over 1 ml columns of DE-52 (Whatman) equilibrated with buffer B. The enzyme was applied to the column and washed with 2×3 ml buffer B. Elution of PKC was then effected by the addition of 2 ml buffer B containing 100 mM NaCl.

Protein Kinase C Assay

PKC was quantitated as described in Thomas et al., ibid. The assay contained 20 mM Tris (pH 7.5), 0.75 mM CaCl, 10 mM magnesium acetate, 0.1 g/ml histone III-S, 0.25 µg/ml leupeptin, 100 µM [gamma-$^{32}$p]-ATP (120 cpm/pmol), 0.96 µg/ml phosphatidylserine, and 0.0064 µg/ml 1,2-diolein in a total assay volume of 250 µl. Blanks contained no calcium or phospholipids. Incubation was for 5 minutes at 30° C. at which point the reaction was terminated by the addition of 1 ml 25% trichloroacetic acid (TCA). Samples were applied to Whatman GF/B filters, the tube rinsed twice with 5% TCA and the filter then washed 5 times with 5% TCA.

Adhesion of B16F1 Cells to Basement Membrane Proteins

Adhesion proteins (2 µg/well) were coated onto Immulon I Removawells from Dynatech and incubated for 1 hour at 37° C. The wells were then blocked for 1 hour with 400 µl PBS, pH 7.2 containing 1% bovine serum albumin (BSA) at 37° C. Prior to addition of the cell suspension, the blocking solution was aspirated.

Sub-confluent cells were washed twice with HBSS and removed form flasks by incubation for 10 minutes at 37° C. with PBS (pH 7.2), 2 mM EDTA, and 1% BSA. The cells were washed twice with MEM containing 20 mM HEPES and 0.1% BSA and resuspended in the same medium to give a cell density of $1\times10^5$ cells/ml.

Cells were added to wells in 50 μl ($5\times10^4$ cells) and incubated at 37° C. The wells were aspirated and washed three times with 400 μl PBS (pH 7.2) containing 0.1% BSA. Wells were detached and counted in 5 ml Beckman Ready Protein. Blanks were not coated with protein but were blocked with BSA as described above.

Adhesion of Tumor Cells to Endothelial Cells

Round 15 mm Thermanox tissue culture cover slips from Lux were placed in Corning 12-well, 22 mm diameter tissue culture clusters. HUVEC ($2\times10^6$) were added to each well and grown to confluency. Sub-confluent B16F1 cells were labeled with 1 μCi/ml [$^3$H]-thymidine (New England Nuclear, 78.5 Ci/mmol) for 24 hours at 37° C.

In preparation for the adhesion assay, the tissue culture wells containing either HUVEC or no cells were blocked with MEM containing 20 mM HEPES and 1% BSA for 1 hour at 37° C. B16F1 cells were removed from the flasks as described above for adhesion to basement membrane proteins and diluted to a density of $2\times10^5$ viable cells/ml in MEM (viability determined by trypan blue exclusion).

Blocking solution was aspirated from the wells and 1 ml of cells were added per well and incubated at 37° C. Nonadherent cells were washed from coverslips as described in Wright, P. S., Cross-Doersen, D., McCann, P. P. and Bitonti, A. J., *Plasmodium falciparum*: a rapid assay for cytoadherence of [$^3$H]-hypoxanthine-labeled infected erythrocytes to human melanoma cells, *Exp. Parasitol.*, 71: 346–349, 1990. Coverslips were retrieved from the well with forceps and dipped 10 times into a beaker of 100 ml MEM. Coverslips were placed into scintillation vials and counted in 10 ml Beckman Ready Protein.

TABLE 1

EFFECTS OF 4-PROPYL-5(4-PYRIDINYL)-2(3H)-OXAZOLONE ON B16F1 COLONY FORMATION
B16F1 cells ($10^2$) were plated and incubated for 24 hours at 37° C. Next, 4-propyl-5(4-pyridinyl)-2(3H)-oxazolone (compound 1) was added and incubation continued for an additional 24 hours at which time the drug was removed. Ten days later, colonies greater than 2 mm in diameter were counted.

| Treatment | Colonies per dish | Mean +/− SE |
|---|---|---|
| None | 21, 27, 30 | 26 +/− 3 |
| 10 μM compound 1 | 24, 26, 31 | 27 +/− 2 |
| 20 μM compound 1 | 31, 34, 36 | 34 +/− 1 |
| 50 μM compound 1 | 28, 29, 31 | 29 +/− 1 |

TABLE 2

INHIBITION OF EXPERIMENTAL METASTASIS OF B16F1 CELLS BY 4-PROPYL-5(4-PYRIDINYL)-2(3H)-OXAZOLONE
Sub-confluent B16F1 cells were incubated with 4-propyl-5(4-pyridinyl)-2(3H)-oxazolone (compound 1) for 24 hours at 37° C. Cells were then harvested and $1\times10^5$ cells were injected intravenously into mice. Three weeks later, metastatic nodules were counted as described in Material and Methods.

| Treatment With Compound 1 | Number of nodules per set of lungs | Mean +/− SE | % Control |
|---|---|---|---|
| None | 27, 13, 13, 13, 19, 10, 31 | 18 +/− 3.3 | 100 |
| 1 μM | 7, 18, 2, 21, 9, 8, 18 | 12 +/− 2.8 | 67 |

TABLE 2-continued

INHIBITION OF EXPERIMENTAL METASTASIS OF B16F1 CELLS BY 4-PROPYL-5(4-PYRIDINYL)-2(3H)-OXAZOLONE
Sub-confluent B16F1 cells were incubated with 4-propyl-5(4-pyridinyl)-2(3H)-oxazolone (compound 1) for 24 hours at 37° C. Cells were then harvested and $1\times10^5$ cells were injected intravenously into mice. Three weeks later, metastatic nodules were counted as described in Material and Methods.

| Treatment With Compound 1 | Number of nodules per set of lungs | Mean +/− SE | % Control |
|---|---|---|---|
| 5 μM | 8, 20, 8, 7, 8, 25, 22 | 14 +/− 3.3 | 78 |
| 10 μM | 3, 7, 8, 7, 15, 14, 1 | 7.8 +/− 2.1 | 43 |
| 20 μM | 8, 2, 5, 7, 2, 8, 6 | 5.4 +/− 1.1 | 30 |
| 50 μM | 0, 4, 2, 2, 2, 4, 1 | 2 +/− 0.6 | 12 |

TABLE 3

EFFECTS OF PKC INHIBITORS ON B16F1 PKC ACTIVITY AND EXPERIMENTAL METASTASIS

| Treatment | PKC Activity[a] $IC_{50}$, μM Cytosol | Membrane | B16 Metastasis[b] $IC_{50}$, μM |
|---|---|---|---|
| Compound 1 | 54 | 13 | 6.8 |
| Compound 2[c] | 500 | 250 | 36 |
| Compound 3[d] | 47 | 15 | 68 |
| Compound 4[e] | 62 | 94 | N.D.[f] |
| Staurosporine | 0.019 | 0.025 | 0.03 |
| H-7 | 180 | 71 | 12.5 |

[a]Sub-confluent B16F1 cells were harvested and cytosol and membrane fractions prepared as described in Materials and Methods. PKC activity was then measured in the presence of the drugs listed.
[b]Sub-confluent B16F1 cells were exposed to drugs for 24 hours at 37° C. Cells were then harvested and $1\times10^5$ cells injected intravenously into mice. The number of metastatic nodules were quantitated three weeks later.
[c]Compound 2 is 4-methyl-5-(4-pyridinyl)-2(3H)-oxazolone.
[d]Compound 3 is 4-ethyl-5-(4-quinolinyl)-2(3H)-oxazolone.
[e]Compound 5 is 4-propyl-5-(4-quinolinyl)-2(3H)-oxazolone.
[f]N.D., not determined.

TABLE 4

PKC ACTIVITY IN CYTOSOL AND MEMBRANES OF B16F1 CELLS PRETREATED WITH 4-PROPYL-5(4-PYRIDINYL)-2(3H)-OXAZOLONE
B16F1 cells were incubated with 4-propyl-5(4-pyridinyl)-2(3H)-oxazolone for 24 hours at 37° C. PKC was then prepared and its activity was measured as described in Materials and Methods.

| Treatment | PKC Activity pmol per min cytosol | per mg protein membrane | Ratio membrane/cytosol |
|---|---|---|---|
| None | 4541 | 1934 | 0.42 |
| 5 μM compound 1 | 7305 | 2151 | 0.29 |
| 25 μM compound 1 | 2485 | 1511 | 0.61 |
| 50 μM compound 1 | 3658 | 1000 | 0.27 |

TABLE 5

INHIBITION OF B16F1 MELANOMA CELL ADHESION
TO ENDOTHELIAL CELLS (HUVEC)
B16F1 cells were treated with 4-propyl-5(4-pyridinyl)-
(3H)-oxazolone for 24 hours at 37° C. Cells were then
harvested and added to wells containing confluent HUVEC
cells and incubated for the time indicated at 37° C. Details
are given in Materials and Methods.

| | Adherent B16F1 Cells[a] | |
|---|---|---|
| Time, min | Control | 50 μM 4-propyl-5 (4-pyridinyl)- 2(3H)-oxazolone |
| 5 | 3,593 +/− 913 | 4,513 +/− 1,773 (126)[b] |
| 10 | 20,014 +/− 1,328 | 7,828 +/− 1,422 (39) |
| 20 | 79,400 +/− 10,901 | 48,750 +/− 7,024 (60) |
| 30 | 130,021 +/− 6,541 | 92,084 +/− 5,386 (71) |
| 60 | 124,979 +/− 10,669 | 136,950 +/− 6,341 (110) |

[a]Mean +/− SE
[b]Values in parentheses represent B16F1 cells adhered expressed as percent of control.

The term "patient" used herein is taken to mean mammals such as primates, including humans, sheep, horses, cattle, pigs, dogs, cats, rats and mice.

The amount of the oxazolone derivative of formula 1 to be administered can vary widely according to the particular dosage unit employed, the period of treatment, the age and sex of the patient treated, the nature and extent of development of the lung tumor to be treated, and the particular oxazolone derivative selected. The amount of a oxazolone derivative of formula 1 effective to inhibit metastasis in patients having lung cancer will generally range from about 15 mg/kg to 500 mg/kg. A unit dosage may contain from 25 to 500 mg of the oxazolone derivative, and can be taken one or more times per day. The oxazolone derivative can be administered with a pharmaceutical carrier using conventional dosage unit forms either orally or parenterally.

The preferred route of administration is oral administration. For oral administration the oxazolone derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the breakup and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the esthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The oxazolone derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethylene-glycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quaternary ammonium salts, as well as mixtures. The parenteral compositions of this invention will typically contain from about 0.5 to about 25% by weight of the oxazolone derivative of formula 1 in solution. Preservatives and buffers may also be used advantageously. In order to minimize or eliminate irritation at the site of injection, such compositions may contain a nonionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The following specific examples are presented to illustrate the synthesis of the compounds of this invention, but they should not be construed as limiting the scope of this invention in any way.

EXAMPLE 1

4-Ethyl-5(4-Pyridinyl)-2(3H)-Oxazolone

First, 1-hydroxy-2-(4-pyridyl)butan-2-one (26.4 g, 0.16 mol) was dissolved in 350 ml of 2N HCl. Potassium cyanate (38.9 g, 0.48 mol) was added portionwise to this solution over a period of one hour with stirring. After the addition was complete, concentrated hydrochloric acid was added until the pH of the solution was one. After an additional hour the reaction mixture was made basic by addition of sodium bicarbonate solution and the resulting mixture was stirred overnight. The resulting solid precipitate was collected and recrystallized twice from 50% aqueous ethanol to yield the title compound (14.4 g, 47% of theoretical yield), m.p. 287°–289° C. (dec.).

Using the procedure above but using 1-(hydroxy)-1-(4-pyridyl)pentan-2-one or 1-(hydroxy)-1-(4-pyridyl)-propan-2-one instead of 1-hydroxy-1-(4-pyridyl)butan-2-one results in 4-propyl-5(4-pyridinyl)-2(3H)-oxazolone, m.p. 257°–259° C. (dec.) or 4-methyl-5(4-pyridinyl)-2(3H)-oxazolone, m.p.<310° C.

EXAMPLE 2

4-Ethyl-5(2-Pyridyl)-2(3H)-Oxazolone

Potassium cyanate (35.4 g, 0.44 mol) was added to a solution of 2-hydroxy-1-(2-pyridyl)butan-1-one (31 g, 0.15 mol) in 250 ml of 2N HCl diluted with 300 ml of water. After 1 hour the acidity was adjusted (pH=1) with concentrated hydrochloric acid and then allowed to stir overnight. The mixture was made basic by addition of aqueous sodium bicarbonate. The resulting gummy precipitate was chromatographed on silica gel and recrystallized twice from 50% aqueous ethanol to give the title compound, m.p. 196°–197° C. (dec.).

In a manner substantially similar to that of Examples 1 and 2, the compounds 4-phenyl-5(4-pyridinyl)-2(3H)oxazolone (mp>300° C.) and 4-propyl-5-(2-phenylpyridin-4-yl)-2(3H)-oxazolone (mp 202°–204° C.) were prepared.

EXAMPLE 3

A tablet is prepared from

| | |
|---|---|
| 4-propyl-5(4-pyridinyl)-2(3H)-oxazolone | 250 mg |
| starch | 40 mg |
| talc | 10 mg |
| magnesium stearate | 10 mg |

EXAMPLE 4

A capsule is prepared from

| | |
|---|---|
| 4-ethyl-5(4-pyridin)yl-2(3H)-oxazolone | 400 mg |
| talc | 40 mg |
| sodium carboxymethylcellulose | 40 mg |
| starch | 120 mg |

EXAMPLE 5

A tablet is prepared from

| | |
|---|---|
| 4-methyl-5(3-pyridinyl)-1-(3H)-oxazolone | 250 mg |
| Starch | 40 mg |
| Talc | 10 mg |
| Magnesium | 10 mg |

EXAMPLE 6

A capsule is prepared from

| | |
|---|---|
| 4-phenyl-5(2-pyridinyl)1-(3H)-oxazolone | 400 mg |
| Talc | 40 mg |
| Sodium Carboxymethyl cellulose | 40 mg |
| Starch | 120 mg |

It should be apparent to one of ordinary skill in the art that changes and modifications can be made to this invention without departing from the spirit or scope of the invention as it is set forth herein.

What is claimed is:

1. A method of inhibiting metastasis in a patient having metastatic lung cancer which comprises administering to the patient an amount of a compound of the formula I effective to inhibit metastasis

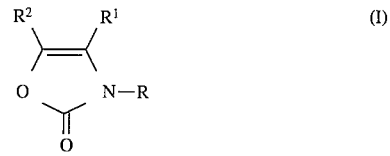

wherein

R and $R^1$ are each independently selected from the group consisting of hydrogen, $C_1$–$C_6$ alkyl, and phenyl or $C_1$–$C_3$ alkylphenyl wherein the phenyl ring is optionally substituted with one, two or three of the substituents selected from the group consisting of fluorine, chlorine, bromine, $C_1$–$C_4$ alkyl, and $C_1$–$C_4$ alkoxy; and $R^2$ is a 2-, 3-, or 4-pyridyl group wherein the pyridyl group is optionally substituted with one or two substituents selected from the group consisting of fluorine, chlorine, bromine, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, cyano, carboxy, carb($C_1$–$C_5$)alkoxy, carbamido, ($C_1$–$C_5$)alkanoylamino, imidazolyl, nitro and trifluoromethyl or wherein the pyridyl group is optionally substituted with a phenyl group which is optionally substituted with one, two or three of the substituents selected from the group consisting of fluorine, chlorine, bromine, $C_1$–$C_4$ alkyl, and $C_1$–$C_4$ alkoxy;

or a pharmaceutically-acceptable salt thereof.

2. A method of claim 1 wherein $R^2$ is an optionally substituted 2-, 3-, or 4-pyridyl group.

3. A method of claim 2 wherein R and $R^1$ are each independently selected from the group consisting of hydrogen or $C_1$–$C_6$ alkyl.

4. A method of claim 3 wherein R is $C_1$–$C_6$ alkyl and $R^1$ is hydrogen.

5. A method of claim 4 wherein $R^2$ is an unsubstituted 2-, 3-, or 4-pyridyl group.

6. A method of claim 5 wherein $R_2$ is 4-pyridyl, R is propyl, and $R^1$ is hydrogen.

7. A method of claim 1 wherein the compound is 4-propyl-5(4-pyridinyl)-2(3H)-oxazolone.

\* \* \* \* \*